US012748045B2

(12) United States Patent
Weigel et al.

(10) Patent No.: US 12,748,045 B2
(45) Date of Patent: Sep. 29, 2026

(54) APPARATUS AND METHOD FOR A MEASUREMENT OF A SPECTRAL RESPONSE OF A SAMPLE, INCLUDING A QUANTUM-CASCADE-LASER-BASED LIGHT AMPLIFICATION

(71) Applicants: Molekuláris-Ujjlenyomat Kutató Központ Nonprofit Kft, Budapest (HU); Max-Planck-Gesellschaft Zur Förderung Der Wissenschaften E.V., Munich (DE); Ludwig-Maximilians-Universität München, Munich (DE)

(72) Inventors: Alexander Weigel, Munich (DE); Qu Shizhen, Munich (DE); Ka Fai Mak, Munich (DE); Ferenc Krausz, Garching (DE)

(73) Assignees: Molekuláris- Ujjlenyomat Kutató Kózpont Nonprofit Kft., Budapest (HU); Max-Planck-Gesellschaft Zur Förderung Der Wissenschaften E.V., Munich (DE); Ludwig-Maximilians-Universität München, Munich (DE)

( * ) Notice: Subject to any disclaimer, the term of this patent is extended or adjusted under 35 U.S.C. 154(b) by 85 days.

(21) Appl. No.: 18/564,277

(22) PCT Filed: May 27, 2021

(86) PCT No.: PCT/HU2021/050030

§ 371 (c)(1),
(2) Date: Nov. 27, 2023

(87) PCT Pub. No.: WO2022/248894

PCT Pub. Date: Jan. 12, 2022

(65) Prior Publication Data

US 2024/0255421 A1 Aug. 1, 2024

(51) Int. Cl.
*G01N 21/3563* (2014.01)
*G01N 33/483* (2006.01)

(52) U.S. Cl.
CPC ..... *G01N 21/3563* (2013.01); *G01N 33/4833* (2013.01); *G01N 2201/06113* (2013.01)

(58) Field of Classification Search
None
See application file for complete search history.

(56) References Cited

U.S. PATENT DOCUMENTS

2009/0073432 A1* 3/2009 Jalali .................... G01N 21/65 356/301
2015/0292947 A1* 10/2015 Kotidis ............. G02B 21/0028 356/402

FOREIGN PATENT DOCUMENTS

EP 3237883 B1 8/2020
JP 2009246345 A 10/2009
(Continued)

OTHER PUBLICATIONS

European Patent Office, International Search Report in PCT Application No. PCT/HU2021/050030, mailed on Jan. 25, 2022 (3 pgs.) and Written Opinion Of The international Searching Authority (4 pgs.).
(Continued)

*Primary Examiner* — Marcus H Taningco
(74) *Attorney, Agent, or Firm* — Wood Herron & Evans LLP

(57) ABSTRACT

A spectroscopic measuring apparatus (100) being configured for measuring a spectral response of a sample (1), in particular a biological sample, comprises a fs laser source device (10) being arranged for an irradiation of the sample (1) with a sequence of probe light pulses (2) having a primary spectrum, a detector device (20) being arranged for a temporally and/or spectrally resolved detection of response
(Continued)

light pulses (2') having an altered spectrum and/or temporal structure and resulting from an interaction of the probe light pulses (2) with the sample (1), and a pulse modification device (30) comprising at least one quantum cascade laser ($\mathbf{3}_1$ . . . $\mathbf{3}_N$), wherein the pulse modification device (30) is configured to modify at least one of the probe light pulses (2) and the response light pulses (2') by amplifying one or more spectral components of the at least one of the probe light pulses (2) and the response light pulses (2') with the at least one quantum cascade laser ($\mathbf{3}_1$ . . . $\mathbf{3}_N$). Furthermore, a method of measuring a spectral and/or temporal response of a sample (1), preferably a biological sample, is described.

18 Claims, 5 Drawing Sheets

(56) References Cited

FOREIGN PATENT DOCUMENTS

| | | |
|---|---|---|
| JP | 2018500568 A | 1/2018 |
| JP | 2020512553 A | 4/2020 |

OTHER PUBLICATIONS

Time-domain spectroscopy of mid-infrared quantum cascade lasers, Wolfgang Parz et al., IOP Publishing, Semiconductor science and technology, vol. 26(1), Nov. 29, 2010 (Nov. 29, 2010) doi: 10.1088/0268-1242/26/1/014020 (Still trying to obtain).

Application No. EP 21 94 2855, Supplemental European Search Report and Opinion, Feb. 14, 2025.

Japanese Application No. 2023-57325 Office Action dated Jun. 7, 2025.

Bachmann D. et al: "Amplification of broadband terahertz pulses in a quantum cascade heterostructure", 2015 Conference On Lasers and Electro-Optics(CLEO), OSA, May 10, 2015, (May 10, 2015), pp. 1-2.

Maysonnave J. et al:"Integrated injection seeded terahertz source and amplifier for time-domain spectroscopy", Optics Letters, Optical Society of America, US, vol. 37, No. 4, Feb. 15, 2012(Feb. 15, 2012), pp. 731-733.

Dhillon S.S. et al: "Ultrafast gain switching of THz quantum cascade lasers", Ultrafast Phenomena in Semiconductors and Nanostructure Materials XV, SPIE, 1000 20TH St. Bellingham WA 98225-6705 USA, vol. 7937,No. 1, Feb. 10, 2011(Feb. 10, 2011), pp. 1-7.

Rakic Aleksandar D. et al: "Swept-frequency feedback interferometry using terahertz frequency QCLs: a method for imaging and materials analysis", Optics Express, vol. 21, No. 19, Sep. 12, 2013(Sep. 12, 2013), p. 22194.

Cheville R.A. et al:"Far-Infrared Terahertz Time-Domain Spectroscopy Of Flames", Optics Letters, Optical Society of America, US, vol. 20, No. 15, Aug. 1, 1995(Aug. 1, 1995), pp. 1646-1648.

Jukam N. et al.: "Terahertz amplifier based on gain switching in a quantum cascade laser", Conference On Lasers and Electro-Optics (CLEO) and Quantum Electronics and Laser Science Conference (QELS), 2010: May 16-21, 2010, San Jose, CA, USA, IEEE, Piscataway, NJ, USA, May 16, 2010 (May 16, 2010), pp. 1-2.

Lim Yah Leng et al: "Coherent imaging using laser feedback interferometry with pulsed-mode terahertz quantum cascade lasers", Optics Express, vol. 27, No. 7, Mar. 28, 2019 (Mar. 28, 2019), p. 10221.

* cited by examiner

APPARATUS AND METHOD FOR A MEASUREMENT OF A SPECTRAL RESPONSE OF A SAMPLE, INCLUDING A QUANTUM-CASCADE-LASER-BASED LIGHT AMPLIFICATION

This application claims priority, as a continuation under Section 120, to PCT Application No. PCT/HU2021/050030, filed May 27, 2021, which is expressly incorporated by reference herein, in its entirety.

TECHNICAL FIELD

The invention relates to a method of measuring a spectral response of a sample and a spectroscopic measuring apparatus being configured for measuring a spectral response of a sample. In particular, the invention relates to a method of measuring the spectral response by irradiating the sample with broadband mid-infrared probe light and sensing changes of the probe light spectral content and/or temporal structure, resulting from an interaction of the probe light with the sample. In addition, the invention relates, in particular, to a spectroscopic measuring apparatus including a broadband mid-infrared light source for irradiating the sample with probe light and a detector device for detecting changes of the probe light resulting from an interaction of the probe light with the sample in spectral and/or time domains. Applications of the invention are available in spectroscopy, in particular high dynamic range field-resolved infrared spectroscopy, of a sample, e.g. a biological sample or another sample having an IR response, in particular for analysing a (molecular) composition of a sample and/or changes thereof.

BACKGROUND ART

For illustrating background art relating to the invention, reference is made to the following prior art documents:

[1] Lasch, P. & Kneipp, J. Biomedical Vibrational Spectroscopy (Wiley, 2010);

[2] Pupeza, Ioachim, et al. “Field-resolved infrared spectroscopy of biological systems” Nature 577, 7788, 52-59 (2020);

[3] Zhang, Jinwei, et al. “Intra-pulse difference-frequency generation of mid-infrared (2.7-20 μm) by random quasi-phase-matching” Optics Letters 44, 12, 2986-2989 (2019);

[4] Wang, Qing, et al. “Broadband mid-infrared coverage (2-17 μm) with few-cycle pulses via cascaded parametric processes” Optics Letters 44, 10 (2019): 2566-2569;

[5] Novák, Ondřej, et al. “Femtosecond 8.5 μm source based on intrapulse difference-frequency generation of 2.1 μm pulses” Optics Letters 43, 6, 1335-1338 (2018);

[6] Williams, B. “Terahertz quantum-cascade lasers” Nature Photonics 1, 517-525 (2007);

[7] Rauter, Patrick, et al. “Multi-wavelength quantum cascade laser arrays” Laser & Photonics Reviews 9.5, 452-477(2015);

[8] Zhu, Huan, et al. “Terahertz master-oscillator power-amplifier quantum cascade laser with a grating coupler of extremely low reflectivity” Optics Express 26, 2, 1942-1953 (2018);

[9] Zhou, Wenjia, et al. “Single-mode, high-power, mid-infrared, quantum cascade laser phased arrays” Scientific Reports 8, 1, 1-6 (2018);

[10] Andriukaitis, Giedrius, et al. “90 GW peak power few-cycle mid-infrared pulses from an optical parametric amplifier” Optics Letters 36, 15, 2755-2757 (2011);

[11] Seidel, Marcus, et al. “Multi-watt, multi-octave, mid-infrared femtosecond source” Science advances 4, 4, eaaq1526 (2018);

[12] Jukam, Nathan, et al. “Terahertz amplifier based on gain switching in a quantum cascade laser” Nature Photonics 3, 12 (2009): 715-719;

[13] Bachmann, Dominic, et al. “Broadband terahertz amplification in a heterogeneous quantum cascade laser” Optics Express 23, 3 (2015): 3117-3125;

[14] Oustinov, Dimitri, et al. “Phase seeding of a terahertz quantum cascade laser” Nature communications 1.1 (2010): 1-6; and

[15] Schubert, Olaf, et al. “Rapid-scan acousto-optical delay line with 34 kHz scan rate and 15 as precision” Optics Letters 38, 15 (2013): 2907-2910.

It is generally known that broadband infrared spectroscopy can distinguish changes in molecular composition of a complex sample by detecting the variation of absorptions in the spectral range from 400 $cm^{-1}$ to 3300 $cm^{-1}$ or 3 μm to 25 μm (so-called molecular fingerprint absorptions), making it an ideal metrology for biomedical sensing [1].

It has recently been shown that field-resolved spectroscopy (FRS) based on femtosecond mid-infrared (MIR) laser pulses can achieve higher dynamic range, sensitivity and specificity for molecular detection when compared to current state-of-the-art Fourier transform infrared (FTIR) spectroscopy [2]. In FRS, a few-optical-cycle, broadband MIR pulse excites the sample, and the full electric field including the molecular response in the wake of the pulse is directly captured in a time-domain electro-optic sampling (EOS) measurement. Despite its success and the prospect to reach multi-octave spectral coverage in future, FRS still faces in particular the following limitations:

i. The intensity of the MIR driving pulses and the corresponding strength of the molecular response are limited by the low efficiency of the nonlinear MIR generation processes. For example, for intra-pulse difference frequency generation (IPDFG) that provides particularly phase-stable pulse, the efficiency is only 0.1% to 3% [3-5];

ii. The current achievable optical signal/noise ratios start to reach the dynamic range limitations of detection electronics [2]; and iii. MIR generation generally relies on phase matching in nonlinear crystals, which produces spectra with non-uniform spectral density across the targeted wavelength range.

There is a need to overcome the limitations to better employ the potential of the FRS or other high-dynamic-range/high-sensitivity techniques.

DESCRIPTION OF THE INVENTION

The objective of the invention is to provide an improved apparatus and method for measuring a spectral response of a sample, e. g., for measuring the molecular composition and/or changes in the molecular composition of the sample, which avoids disadvantages of conventional techniques. In particular, the objective of the invention is to provide a method and a measuring apparatus for measuring a spectral response of a sample with an increased sensitivity, improved signal-to-noise-ratio (SNR), enhanced selectivity, improved uniformity of the spectral density across a targeted wavelength range and/or improved capability of covering an extended spectral range, e.g., in the mid-infrared spectral range (MIR).

These objectives are solved by the subject matter of the independent claims. Preferred embodiments and applications of the invention are defined in the dependent claims.

According to a first general aspect of the invention, a spectroscopic measuring apparatus is provided. The spectroscopic measuring apparatus is configured for measuring a spectral response of a sample, e.g., a biological sample or another sample with an IR response. To this end, the spectroscopic measuring apparatus comprises a femtosecond (fs) laser source device (e.g., including a Ho-YAG laser, an Yb:YAG thin-disk laser, a Ti:Sa laser, an Er:fiber laser or a Cr:ZnS laser) being arranged for an irradiation of the sample with a sequence of probe light pulses having a primary spectrum. Preferably, the primary spectrum—i.e., the spectral composition of the probe light pulses—is a continuous or quasi-continuous spectrum in the mid-infrared range. For example, the primary spectrum may cover the wavelength range from 5 μm to 15 μm. Further, the spectroscopic measuring apparatus comprises a detector device (e.g., an FTIR-spectrometer; preferably field-resolved detection with EOS) being arranged for a spectrally and/or temporally resolved detection of response light pulses having an altered spectrum and/or temporal structure and resulting from an interaction of the probe light pulses with the sample. Each of the response light pulses results from one of the probe light pulses interacting with the sample. In other words, the detector device may be arranged to measure the spectral composition and/or temporal profile of the modified probe light pulses (i. e., the response light pulses), whose spectra and/or temporal structures may differ from that of the initial probe light pulses due to light-matter interactions (e.g., excitation of vibrational and/or rotational molecular states of the sample) and may be used, for example, for analysing the molecular composition of the sample.

In addition, according to the invention, the claimed spectroscopic measuring apparatus further includes a pulse modification device comprising at least one quantum cascade laser (QCL). This type of laser is basically known in the prior art and refers to a (inter-subband) semiconductor laser emitting around a centre wavelength ranging in the mid-infrared (e.g., from 3 μm to above 24 μm) with, e. g., up to several Watts of output power. Advantageously, the emission properties of QCLs can be designed by creating specific quantum well structures with semiconductor-multilayer sequences, providing a plethora of powerful and customizable on-chip lasers [6, 7].

According to the invention, the pulse modification device is configured to modify the probe light pulses and/or the response light pulses by amplifying one or more spectral components of the probe light pulses and/or the response light pulses with the at least one quantum cascade laser. In other words, the pulse modification device may be configured to modify the probe light pulses before reaching, in particular interacting with, the sample, and/or to modify the response light pulses before entering the detector device. As described in detail below, the use of the QCL technology within the claimed spectroscopic measuring apparatus advantageously allows for boosting the power of the probe light pulses from the usual tens-of-milli-Watt regime (see, e.g., [2]) to a multi-Watt level, increasing the molecular response and leading to a higher detected signal/noise and hence higher sensitivity. A further advantage of the claimed pulse modification device is that it may allow for shaping the primary spectrum (e.g., by selectively enhancing specific spectral regions, for example with typical absorption bands), such that each probe light pulse optimally excites the sample. Alternatively, or in addition, the pulse modification device may also be used for time-gated amplification of the probe light pulses and/or the response light pulses, in particular to selectively enhance the molecular response in the wake (tail) of the main (excitation) pulse, thus strongly reducing the demands on the dynamic range of the detector.

The inventors have found, that a QCL, compared with other available amplification techniques, provides in particular the following further advantages, which can be employed in the spectroscopic measurement. The energy conversion in QCLs is very efficient since it allows the re-use of each electron to generate multiple photons. The direct conversion of electric energy into photons and their small size give QCLs also advantages in reaching lower amplification noise compared to, e. g., optical parametric amplifiers (OPAs). In addition, the energy conversion efficiency in the MIR OPA is limited by its low quantum efficiency, defined by the photon energy ratio between MIR output and NIR pump laser. It thus requires high power pump lasers in order to achieve similar output as QCLs. Besides, the OPA requires multiple optical elements and usually takes up much more space than a QCL that implements amplification on a chip.

In the present context, the term "probe light pulse" may generally refer to a light pulse in the optical path between the fs laser source device and the sample, though it may eventually be a "modified probe light pulse" when interacting with the sample. Similarly, the term "response light pulse" may generally refer to a light pulse in the optical path between the sample and the detector device, though it may eventually be a "modified response light pulse" when entering the detector device.

For creating the sequence of probe laser pulses, the fs laser source device preferably is a pulsed fs laser source device which may be configured to generate periodic pulse trains, preferably with a repetition rate in a range from e. g. 100 kHz to 10 MHz or more, e. g., to several hundreds of MHz. Furthermore, it is clear to those skilled in the art that, though the invention is primarily described in the context of sequences of probe/response light pulses, its teaching can also be applied in the context of employing a few or a single probe light pulse(s).

The basic advantage of the invention results from employing one or more quantum cascade lasers for selectively amplifying spectral components of the probe light before reaching the sample and/or for selectively amplifying spectral components of the response light, resulting from the interaction of the probe light with the sample, before reaching the detector. By this, for example, the power of the probe light can be boosted from the usual tens-of-milli-Watt regime (see e.g. [2]) to a multi-Watt level, increasing the molecular response and leading to a higher detected signal/noise and hence higher sensitivity. Additionally, or alternatively, the quantum cascade laser(s) can also be used for modifying the response light, e.g. by selectively enhancing only the molecular response after the main pulse, which results in signal levels of the molecular response similar to the excitation pulse, thus strongly reducing the demands on the dynamic range of the detector.

According to a preferred embodiment of the invention, the at least one quantum cascade laser may comprise an array of multiple (i. e., at least two, e.g., five or up to ten or even more) quantum cascade lasers with different centre wavelengths. In this context, the term "centre wavelength" may be considered as the respective wavelength corresponding to the centre of mass of the spectrum in frequency domain of the QCL. Preferably, the centre wavelengths of the QCLs of the array are evenly distributed in the mid-infrared regime. Since the spectral bandwidth of a single QCL is usually limited to around 5% of the centre wavelength the inventive use of multiple quantum cascade lasers advantageously allows to possibly cover the full spectrum of an ultra-broadband (e.g., a super-octave) mid-infrared pulse.

As a result, the pulse modification device may be used for a section-wise spectral amplification, which advantageously allows for a controlled tailoring of the pulse spectrum (e.g. flattening the spectrum, enhancing the spectral wings, and/or to increase the power spectral density at frequencies of expected molecular resonances).

According to another preferred embodiment of the invention, the multiple quantum cascade lasers of the array may be arranged in a parallel configuration. Like in the context of parallel electrical circuits, the term "parallel" refers to a configuration, where the QCLs are arranged in different optical branches extending between two common nodes in the optical path. Advantageously, this enables simultaneously amplifying different spectral regimes, thus providing a fast and low-loss solution for modifying mid-infrared light pulses.

In addition, or alternatively, the pulse modification device may comprise a splitter device configured to spatially separate a laser beam input into several sub-beams with different spectral intervals. Furthermore, the pulse modification device may comprise a relaying device configured to direct each of the sub-beams to one of the multiple quantum cascade lasers respectively. In other words, the relaying device—which may also be referred to as a guiding or deflecting device in this context—may be configured to guide each of the sub-beams generated by the splitter device to a respective QCL. Preferably, the assignment of the sub-beams to the respective QCLs is based on the spectral interval of the sub-beams, i.e., the middle of each spectral interval may correspond to a centre wavelength of a QLC. Furthermore, the pulse modification device may comprise a combiner device configured to collimate an amplified output of each of the multiple quantum cascade lasers into a single laser beam output. By this, advantageously, a simultaneous amplification of different spectral regimes is enabled, wherein the usually compact chip design of QCLs facilitates a very space-saving implementation of the pulse modification device.

According to an alternative or additional aspect of the invention, the multiple quantum cascade lasers may be arranged in a sequential configuration (or: serial configuration). Like in the context of serial electrical circuits, also here the term "sequential" may refer to a configuration, where the multiple QCLs are connected "in a line" within a single optical path. Alternatively, or in addition, the pulse modification device may also comprise a relaying device configured to direct a laser beam input in a consecutive order to each of the multiple quantum cascade lasers. Advantageously, this allows for a successive amplification or modification of different spectral regimes.

The parallel and sequential configurations can be combined. Thus, according to another aspect of the invention, the pulse modification device may comprise a first QCL-subset and a second QCL-subset, wherein the first QCL-subset of the multiple quantum cascade lasers is arranged in a parallel configuration and the second QCL-subset of the multiple quantum cascade lasers is arranged in a sequential configuration. In other words, some QCLs of the pulse modification device may be arranged in parallel, e.g., for amplifying the respective spectral regimes simultaneously, while some QCLs of the pulse modification device may be arranged sequentially, e.g., for amplifying the respective spectral regimes consecutively. Each of the first and second subset may include different QCLs, or the first and second subset may share at least one QCL. Thereby, the pulse modification device may also comprise the respective devices (splitter device, relaying device, combiner device) mentioned before in the context of the exclusively parallel or sequential configurations.

According to another aspect of the invention, at least one quantum cascade laser has an output power of at least 1 Watt and/or a centre wavelength in the range between 3 μm and 24 μm. If the pulse modification device comprises an array of multiple QCLs, preferably, all QCLs have an output power of at least 1 Watt and/or a centre wavelength in the range between 3 μm and 24 μm, respectively. Advantageously, this allows for boosting the power of the light pulses from the usual tens-of-milli-Watt regime (see e.g. [2]) to a multi-Watt level. The increased power may result in a correspondingly stronger molecular response, leading to a higher detected signal/noise and hence higher sensitivity in the measurement.

In order to advantageously enhance specific regions of a light pulse in the time domain, according to another aspect of the invention, the pulse modification device may be configured to shape a temporal profile of the probe light pulses and/or the response light pulses by time-gated amplifying one or more spectral components of the probe light pulses and/or the response light pulses. In this context, the term "time-gated" refers to a temporal enhancement of the probe and/or response light pulse based on a controlled on/off-switching of the QCL(s) for a predetermined time interval. For this, e.g., a time gate provided by a radio frequency (RF) setup may be used. In an exemplary embodiment, RF pulses may be generated by illuminating a fast photodiode with a fraction of a driving pulse of the fs laser source device used to generate the (mid-infrared) probe light pulses. The power of the—optionally delayed—RF pulse may then be increased by an amplifier so that the QCL(s) can operate above threshold, driven by the RF pulse, wherein the on-switching of the QCL(s) will be synchronized with the probe light pulse.

This time-gated setup advantageously enables for example to amplify a temporal section of the response light pulse (preferably the part following the main excitation), in which the sample response is encoded. In the context of the "temporal section amplification", it should be noted that the response light pulse in a typical FRS measurement usually contains a main pulse, which mainly corresponds to the probe light pulse, and the molecular response in the wake (tail) of the main pulse. Therefore, the onset of the RF pulse is advantageously timed such that amplification starts after the main pulse. By fast switching on and off the RF pulse, the molecular response at the pulse tail may be selectively amplified. Since the time-gated amplification acts on each pulse waveform individually, this implementation is also suited both for multi-shot acquisition, and for a detection scheme that measures the full EOS trace with a single laser shot.

Alternatively, the time-gated setup also advantageously enables a delay-dependent amplification, wherein the time-gated QCL(s) amplification acts on the full pulse waveform, either before or after sample interaction. Thereby, the on/off switching of amplification may be synchronized with the delay in a multi-pulse scanning experiment, like conventional EOS detection. In this context, the spectroscopic measuring apparatus may comprise a delay device (e.g., a mechanical delay stage) configured to delay the driving pulse temporally driving the time gate relative to the probe light pulse.

According to another embodiment of the invention, the spectroscopic measuring apparatus may further comprise a control device. The control device may be configured to control the pulse modification device to generate a predefined, i.e., a previously determined, spectral and/or temporal profile of the at least one of the probe light pulses and the response light pulses. In other words, the control device may be configured to cause the pulse modification device to modify the spectral and/or temporal shape of the probe light pulse and/or the response light pulse in a defined way. Advantageously, this facilitates for example to shape the probe light pulse spectrally and/or temporally such that it optimally excites the sample, e.g. by increasing the power spectral density at frequencies of expected molecular resonances.

According to another advantageous aspect of the invention the fs laser source device may be adapted for generating the probe light pulses with at least one of the following features: The probe light pulses may comprise ultra-broadband mid-infrared pulses. The probe light pulses may have a pulse duration below 100 fs, in particular below 50 fs. The probe light pulses may have an average power above 10 mW, in particular above 100 mW. The primary spectrum of the probe light pulse may cover at least one frequency octave, in particular at least two frequency octaves. The primary spectrum of the probe light pulse may cover a wavelength range from 5 μm to 15 μm, in particular from 3 μm to 30 μm. The primary spectrum of the probe light pulse may be a continuous or quasi-continuous spectrum.

According to a second general aspect of the invention, a method of measuring a spectral response of a sample (e.g., a biological sample) is provided. To this end, the method comprises the step of irradiating the sample with a sequence of probe light pulses generated by a fs laser source device (e.g., including an Yb-YAG laser), wherein the probe light pulses have a primary spectrum. Preferably, the primary spectrum is a continuous or quasi-continuous spectrum in the mid-infrared regime, e.g., covering the wavelength range from 5 μm to 15 μm. Further, the method comprises the step of spectrally resolved detecting a response light pulse by a detector device (e.g., a detector device configured for electro-optic sampling), wherein the response light pulse has an altered spectrum resulting from an interaction of the probe light pulses with the sample. In addition, the method includes the step of modifying the probe light pulses and/or the response light pulses with a pulse modification device. Thereby, the pulse modification device comprises at least one quantum cascade laser, wherein one or more spectral components of the probe light pulses and/or the response light pulses are amplified with the at least one quantum cascade laser. By this, advantageously, the power of the probe light may be boosted from the usual tens-of-milli-Watt regime (see, e.g., [2]) to a multi-Watt level, increasing the molecular response and leading to a higher detected signal/noise and hence higher sensitivity.

Preferably, the method of the second general aspect of the invention or embodiments thereof is executed by the spectroscopic measuring apparatus of the first general aspect of the invention or embodiments thereof.

According to a preferred embodiment of the invention, the probe light pulses are modified before reaching the sample. Alternatively, or in addition the response light pulses are modified before reaching and/or entering the detector device. Advantageously, this allows for a controlled shaping of the probe light pulses, as well as the response light pulses in dependence of the particular requirements in the different parts of the measurement.

According to another aspect of the invention the at least one quantum cascade laser may comprise an array of multiple quantum cascade lasers with different centre wavelengths. For example, the array of multiple QCLs may comprise 2 to 10 or more QCLs. Preferably, the centre wavelengths of the respective QCLs (i.e., the wavelength of each QCL's bandwidth that might be considered its "middle") are evenly distributed in the mid-infrared regime. Advantageously, the pulse modification device enables such a section-wise spectral amplification, which allows for a controlled tailoring of the pulse spectrum (e.g., flattening the spectrum, enhancing the spectral wings, and/or increasing the power spectral density at frequencies of expected molecular resonances).

According to another aspect of the invention the multiple quantum cascade lasers may be arranged in a parallel configuration. Advantageously, this enables simultaneous amplification of different spectral regimes, thus providing a fast and low-loss solution for modifying a mid-infrared light pulse. Alternatively, or in addition, the step of modifying may include the following steps: splitting the probe light pulses and/or the response light pulses by a splitter device into several sub-beams with different spectral intervals; directing each of the sub-beams to one of the several quantum cascade lasers respectively by a relaying device; and collimating an amplified output of each of the multiple quantum cascade lasers into a single laser beam output by a combiner device.

According to another aspect of the invention the multiple quantum cascade lasers may be arranged in a sequential configuration. Alternatively, or in addition, the step of modifying may include the step of directing the probe light pulses and/or the response light pulses in a consecutive order to each of the several quantum cascade lasers by a relaying device. Advantageously, this allows for a successive amplification or modification of different spectral regimes.

According to another aspect of the invention the pulse modification device may comprise a first QCL-subset and a second QCL-subset, wherein the first QCL-subset of the multiple QCLs is arranged in a parallel configuration and the second QCL-subset of the multiple QCLs is arranged in a sequential configuration. In other words, some QCLs of the pulse modification device may be arranged in parallel, e.g. for amplifying the respective spectral regimes simultaneously, while other QCLs of the pulse modification device may be arranged sequential, e.g. for amplifying the respective spectral regimes consecutively. Thereby, the pulse modification device may also comprise the respective devices (splitter device, relaying device, combiner device) mentioned before in the context of the only parallel or sequential configurations.

According to another aspect of the invention the at least one quantum cascade laser may have an output power of at least 1 Watt and/or a centre wavelength in the range between 3 μm and 24 μm. If the pulse modification device comprises an array of multiple QCLs, preferably, all QCLs have an output power of at least 1 Watt and/or a centre wavelength in the range between 3 μm and 24 μm respectively.

According to another aspect of the invention the method may further comprise the step of determining at least one spectral region of interest (e.g., a frequency of an expected molecular resonance of the sample). Preferably, the spectral region of interest may cover a spectral range, in which a characteristic vibrational and/or rotational transition in the sample may be excited. Further, the step of modifying may include increasing a power spectral density in the spectral region of interest. Advantageously, this allows selectively probing molecular fingerprints of expected constituents of the sample.

According to another aspect of the invention the step of modifying may include time-gated amplification of one or more spectral components of the response light pulses for shaping the temporal profile of the response light pulses. As discussed in detail before, this technique advantageously enables to temporally enhance specific regions of the probe light pulses and/or the response light pulses in the time domain by a controlled on/off-switching of the QCL(s). To this end, a time gate provided by a radio frequency (RF) setup may be used, wherein RF pulses (generated by illuminating a fast photodiode with a fraction of a driving pulse of the fs laser source device) are used to trigger the temporal operation of the QCL(s). By this, advantageously a section of each of the temporally extended response light pulse, preferably the molecular response after the main (excitation) pulse, can be selectively enhanced, resulting in signal levels of the molecular response similar to the excitation pulse, thus strongly reducing the demands on the dynamic range of the detector.

According to another aspect of the invention the method may comprise the step of defining a target spectral profile and/or a target temporal profile of the probe light pulses and/or the response light pulses. For example, the target spectral profile may be a spectral profile of a light pulse, where specific spectral regions (e.g., absorption bands, expected molecular resonances, etc.) are enhanced. Further, a target temporal profile may be, for example, a temporal profile of a light pulse, where a specific region of a light pulse in the time domain (e.g. the tail of a pulse) is enhanced. Thereby, the term "target" should be understood such that the respective profile is a profile intended to achieve. In addition, the method may comprise the step of controlling the pulse modification device by a control device based on the defined target spectral and/or temporal profile. In other words, the pulse modification device may be controlled such that it modifies the spectral and/or temporal shape of the probe and/or the response light pulse in order to correspond with the target spectral and/or temporal profile as best as possible. Advantageously, this allows for a controlled shaping of the spectral and/or temporal profile of the light pulses depending on the particular measurement requirements.

According to another aspect of the inventive apparatus or method, the sample may be a biological sample (e.g., a sample from a human or animal organism, a medical sample). In particular, the sample may be, for example, at least one biological cell or part thereof, a cell group or cell culture, or tissue of an organism, a liquid, like, e.g., blood or other body liquids, optionally diluted, an aerosol, like e.g. breath including traces of liquid droplets, a gas and a vapour, e.g., emanating from a biological organism. Preferably, the sample may be a biological sample for diagnostic purposes. In this context, it should, however, be emphasized that the invention is not restricted to the investigation of biological samples, but rather can be implemented with other samples, like, e.g., substance samples from technical processes or environmental samples, that have a light-matter interaction with the probe light pulses.

Further, all features disclosed in this document in connection with the spectroscopic measurement apparatus are also intended to be disclosed and claimable in connection with the method, and vice versa.

BRIEF DESCRIPTION OF THE DRAWINGS

Further advantages and details of the invention are described in the following with reference to the attached drawings, which schematically show in.

MODES FOR CARRYING OUT THE INVENTION

Figure 1:
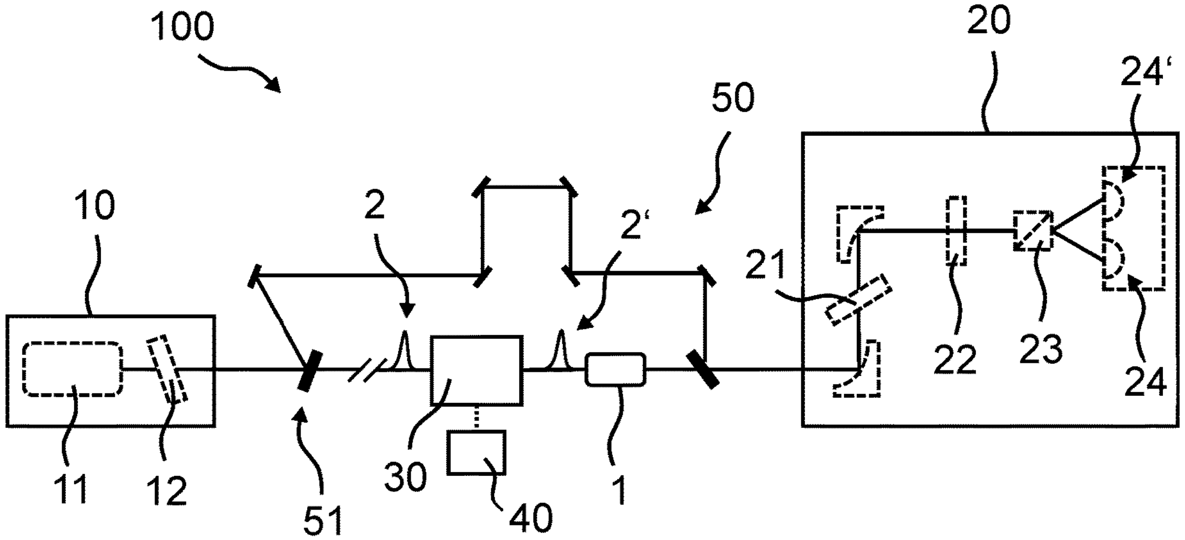
FIG. 1: features of a first embodiment of a spectroscopic measurement apparatus according to the invention.

Features of preferred embodiments of the invention are described in the following with particular reference to the provision of at least one QCL in a spectroscopic measuring setup. Details of QCLs, in particular the configuration and operation thereof, are not described as far as they are known per se from available QCL techniques.

Details of a spectroscopic measuring setup, which are known per se from prior art, like details of FRS, are not described. In the drawings, identical or functionally equivalent elements are labelled with the same reference signs.

FIG. 1 schematically illustrates a first embodiment of the spectroscopic measuring apparatus 100 being configured for measuring a spectral response of a sample 1 according to the invention. The spectroscopic measuring apparatus 100, thereby, comprises a fs laser source device 10 being arranged for an irradiation of the sample 1 with a sequence of probe light pulses 2 having a primary spectrum. Preferably, the probe light pulses 2 are ultra-broadband mid-infrared pulse with a quasi-continuous spectrum. For generating the probe light pulses 2, the fs laser source device 10 may include a driving source 11, like, e.g., an Yb-YAG-disk laser resonator combined with a broadening stage and a chirped mirror compressor, and a difference frequency generation (DFG) unit 12. For example, the driving source 11 may create driving pulses (not shown) with a centre wavelength of 1030 nm, a pulse duration of 250 fs and a repetition rate of 28 MHz, which then enter the DFG unit 12. The DFG unit 12 may be configured to employ intra-pulse difference frequency generation of the input driving pulses by an optically non-linear crystal, like, e.g., a $LiGaS_2$-based crystal, resulting—based on the previous exemplary numbers—in probe light pulses 2 having a primary spectrum ranging from 3 μm to 30 μm (mid-infrared).

Furthermore, the spectroscopic measuring apparatus 100 comprises a detector device 20 being arranged for a spectrally resolved detection of a response light pulse 2' having an altered spectrum resulting from an interaction of the probe light pulse 2 with the sample 1. For this purpose, the detector device 20 may be a (standard) FTIR-spectrometer. However, preferably more sophisticated detector setups are used. As exemplarily shown in FIG. 1, the detector device 20, therefore, may be configured for electro-optic sampling the electric field of the response light pulse 2' in time domain by exploiting the linear electro-optic effect (also called Pockels effect). To this end, the spectroscopic measuring apparatus 100 may comprise a beam splitter element 51, which directs part of the pulses emitted from the laser source device 10 via a delay beam path 50 to the detector device 20.

For example, as illustrated in FIG. 1, the beam splitter element 51 may be a dichroic beam splitting mirror, which is arranged in the beam path between the DFG unit 12 and the sample 1 and exhibits different transmittance/reflectance characteristics in the near-infrared and mid-infrared for separating the initial driving pulses and the generated probe light pulses after the DFG unit 12. Alternatively, the beam splitter element 51 could also be realized as a semi-transparent beam splitting mirror arranged in the beam path between the driving source 11 and the DFG unit 12.

For electro-optically sampling the waveform of the response light pulse 2' in the detector device 20, the response light pulse 2' and a driving pulse—which will be referred to in the following as a sampling pulse—may be spatially recombined and directed into an electro-optic crystal 21 of the detector device 20. The electro-optic crystal 21 can be an optically non-linear crystal, e.g., GaSe, having a $\chi^2$ non-linearity. Thereby, the polarization state of the sampling pulse passing the electro-optic crystal 21 is changed by the electric field of the response light pulses 2'. The sampling pulse with the modified polarization state may pass a half- or quarterwave plate 22 and a Wollaston prism 23 separating sub-pulses and with two orthogonally polarized polarization components of the sampling pulse. These two sub-pulses and carrying the different polarization components are sensed with detector elements 24 and 24', comprising, e.g., photodiodes. Preferably, the detector elements 24 and 24' are balanced, i.e. calibrated such that a difference between the detector signals of the detector elements 24 and 24' is proportional to the electric field of the response light pulse 2'. By iterative measurements, wherein the delay between the two pulses is varied via a delay drive unit (not shown) such that the (short) sampling pulse coincides with different parts of the (longer) response light pulse 2', the full temporal shape of the response light pulse 2' can be recovered. Fourier transforming the temporal shape, i.e. Fourier transforming the detector signal difference, lastly yields the spectral response of the sample 1.

In addition to the above-mentioned components known per se in field of FRS, the claimed spectroscopic measuring apparatus 100 further includes a pulse modification device 30 comprising at least one quantum cascade laser. In the illustrated embodiment, the pulse modification device 30 is configured to modify the probe light pulses 2 before reaching the sample 1 by amplifying one or more spectral components of each of the probe light pulses 2 with the at least one quantum cascade laser. To this end, the modification device 30 is arranged in the beam path between the fs laser source device 10 and the sample 1. Preferably, the modification device 30, thereby, comprises an array, i.e. an arrangement, of multiple (e.g., ten) quantum cascade lasers $\mathbf{3}_1 \ldots \mathbf{3}_N$ with different centre wavelengths $\lambda_1 \ldots \lambda_N$, as described in more in the context of FIG. 3.

In addition to increasing the power of the probe light pulses 2, which may advantageously result in a stronger molecular response, a higher detected signal/noise ratio, and thus a higher sensitivity, the pre-sample amplification also allows for shaping the (primary) spectrum (e.g. by selectively enhancing of specific spectral regions) such that the probe light pulses 2 optimally excite the sample 1.

In this context, the spectroscopic measuring apparatus 100 may also comprise a control device 40 being configured to control the pulse modification device 30 to generate a predefined spectral and/or temporal profile of the probe light pulse 2. For example, the control device 40 may be configured to activate a particular QCL subset of the array of multiple quantum cascade lasers $\mathbf{3}_1 \ldots \mathbf{3}_N$ each for a predetermined time.

Figure 2:
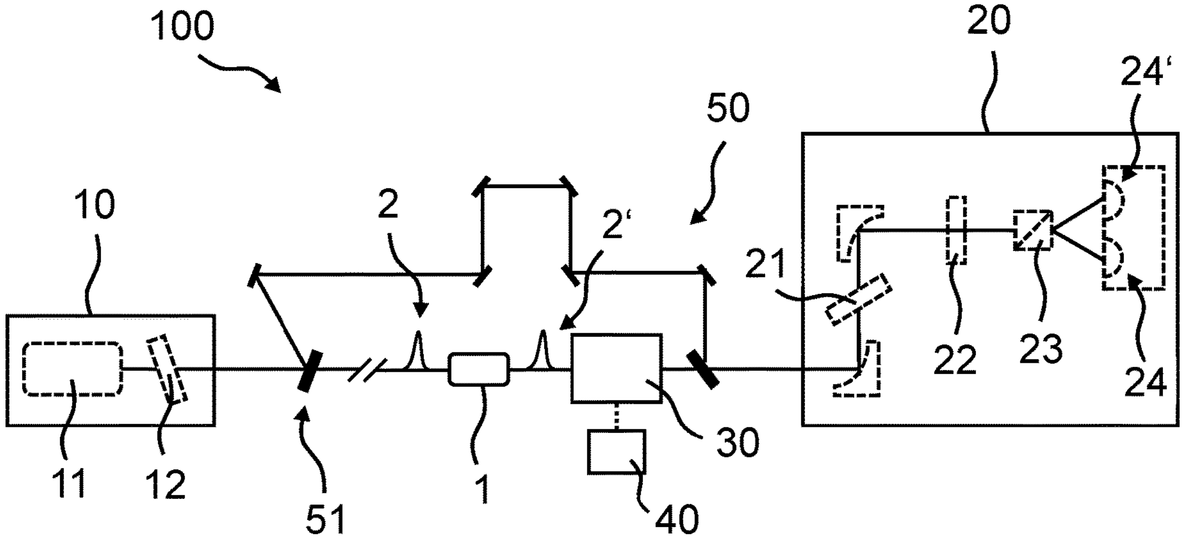
FIG. 2: features of a second embodiment of a spectroscopic measurement apparatus according to the invention.

FIG. 2 schematically illustrates a second embodiment of the spectroscopic measuring apparatus 100 being configured for measuring a spectral response of a sample 1 according to the invention. Different to the embodiment of FIG. 1, which is particularly adapted for modifying the probe light pulse 2 before reaching the sample 1, the spectroscopic measuring apparatus 100 according to FIG. 2 is adapted for modifying the response light pulse 2' before reaching the detector device 20. Accordingly, the pulse modification device 30 comprising at least one quantum cascade laser is arranged in the beam path between the sample 1 and the detector device 20.

Advantageously, the embodiments of FIGS. 1 and 2 enable to perform a time-gated amplification measurement, where at least one section of the temporally extended response light pulse 2', preferably the molecular response after the main (excitation) pulse, is selectively enhanced. This approach, thereby, benefits from the picosecond relaxation dynamics in QCLs that provide an ultrafast switching of the amplification process. In order to control the respective switching of the pulse modification device 30, the spectroscopic measuring apparatus 100 may comprise a control device 40 being configured to control the pulse modification device 30 to generate a predefined temporal profile of the probe light pulse 2 and/or the response light pulse 2'. In particular, the post-sample amplification advantageously allows to raise the molecular signal to similar levels as the excitation pulse, thereby strongly reducing the demands on the dynamic range of the detector. Details of the time-gated amplification are described below with reference to FIGS. 7 and 8.

Figure 3:
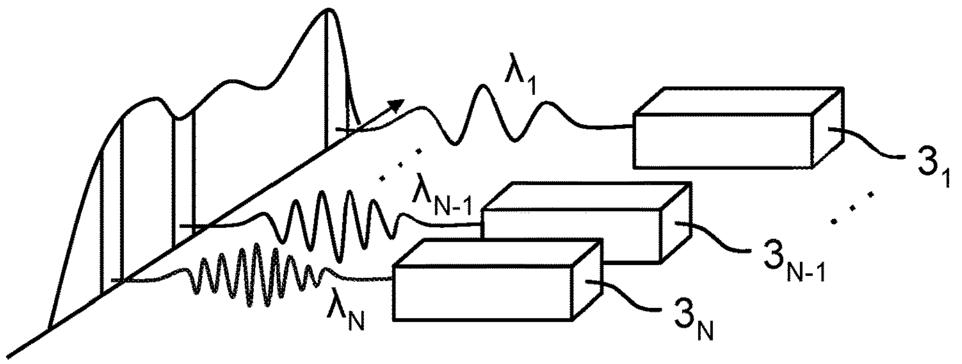
FIG. 3: an illustration of the amplification of spectral components of a mid-infrared light pulse by multiple quantum cascade lasers.

FIG. 3 schematically illustrates the amplification of spectral components of a mid-infrared light pulse, e.g., the afore-mentioned probe light pulse 2 or response light pulse 2', by an array of multiple quantum cascade lasers $\mathbf{3}_1 \ldots \mathbf{3}_N$. The quantum cascade lasers $\mathbf{3}_1 \ldots \mathbf{3}_N$ thereby exhibit narrow wavelength emission around different centre wavelengths $\lambda_1 \ldots \lambda_N$ in the mid-infrared. In this context, the expression "centre wavelength" may be considered as the centre of mass in frequency domain. Preferably, the centre wavelengths $\lambda_1 \ldots \lambda_N$ of the quantum cascade lasers $\mathbf{3}_1 \ldots \mathbf{3}_N$ are evenly distributed in the mid-infrared regime. By varying the output power of each QCLs $\mathbf{3}_1 \ldots \mathbf{3}_N$ individually, the corresponding spectral regions can be differently enhanced, thus advantageously allowing for a controlled modification of the spectral profile of the original mid-infrared light pulse.

Alternatively or in addition to the afore-mentioned modification in the frequency (wavelength) domain, the respective mid-infrared light pulse can be also varied in the time domain. For this, the output power of the QCLs $\mathbf{3}_1 \ldots \mathbf{3}_N$ is individually varied over time, e.g. turned on/off for a predetermined period of time respectively.

While FIG. 3 illustrates the basic principle of the pulse modification, in the following, two specific QCL array arrangements, namely a parallel configuration and a sequential configuration, will be discussed.

Figure 4:
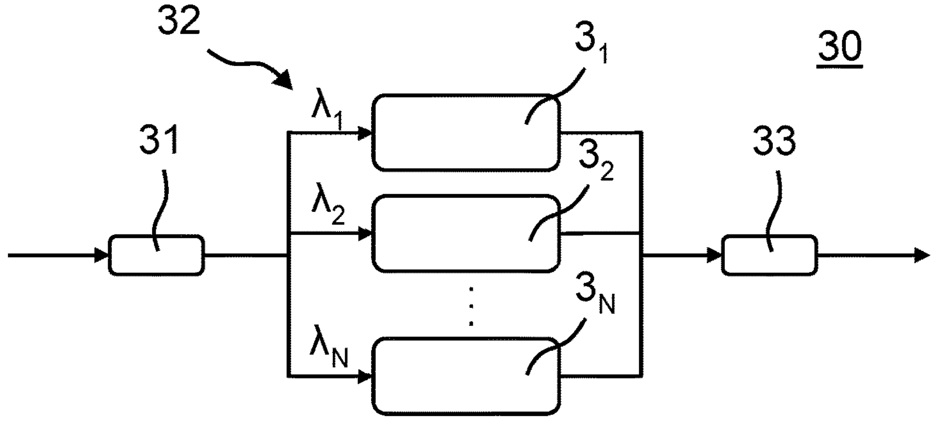
FIG. 4: an illustration of a pulse modification device with an array of multiple quantum cascade lasers arranged in a parallel configuration.

FIG. 4 schematically illustrates a pulse modification device 30 with an array of multiple quantum cascade lasers $\mathbf{3}_1 \ldots \mathbf{3}_N$ arranged in the parallel configuration. For this embodiment, the pulse modification device 30 preferably comprises a splitter device 31 configured to spatially separate a laser beam input into several sub-beams with different spectral intervals. Thereby, the number of spectral intervals may preferably correspond to the number of quantum cascade lasers $\mathbf{3}_1 \ldots \mathbf{3}_N$ and/or the middle of each spectral interval may correspond to a centre wavelength $\lambda_1 \ldots \lambda_N$ of one of the quantum cascade lasers $\mathbf{3}_1 \ldots \mathbf{3}_N$. Furthermore, the pulse modification device 30 may comprise a relaying device 32 (details not shown) configured to direct each of the sub-beams to one of the multiple quantum cascade lasers $\mathbf{3}_1 \ldots \mathbf{3}_N$ respectively. In addition, the pulse modification device 30 may comprise a combiner device 33 configured to collimate an amplified output of each of the multiple quantum cascade lasers $\mathbf{3}_1 \ldots \mathbf{3}_N$ into a single laser beam output.

In total, the parallel configuration with the different optical sub-paths advantageously enables to simultaneously amplify different spectral regimes, thus providing a fast and low-loss solution for modifying a mid-infrared light pulse.

Figure 5:
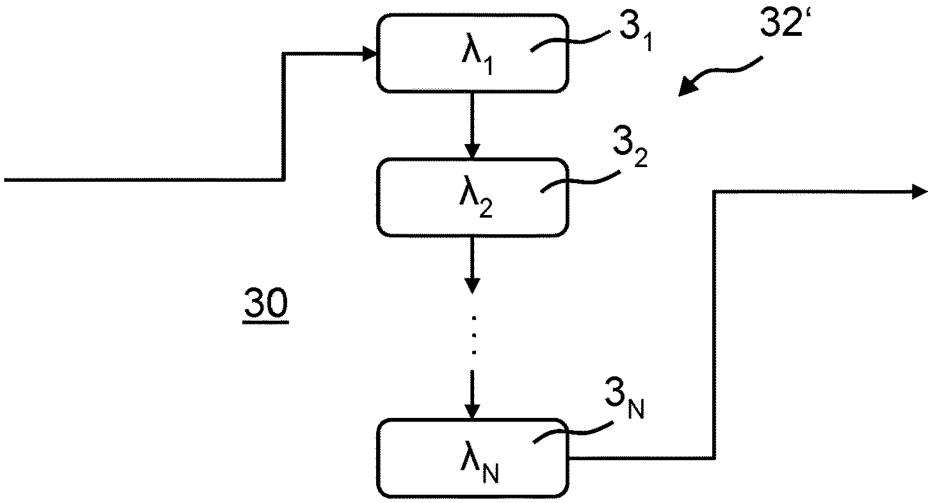
FIG. 5: an illustration of a pulse modification device with an array of multiple quantum cascade lasers arranged in a sequential configuration.

FIG. 5 schematically illustrates a pulse modification device 30 with an array of multiple quantum cascade lasers $\mathbf{3}_1 \ldots \mathbf{3}_N$ arranged in a sequential configuration. For this, the pulse modification device 30 may comprise a relaying device 32' configured to direct a laser beam input in a consecutive order to each of the multiple quantum cascade lasers $\mathbf{3}_1 \ldots \mathbf{3}_N$. In other words, the multiple cascade lasers $\mathbf{3}_1 \ldots \mathbf{3}_N$ are connected "in a line" within a single optical path. As discusses before, the quantum cascade lasers $\mathbf{3}_1 \ldots \mathbf{3}_N$ preferably have different centre wavelengths $\lambda_1 \ldots \lambda_N$, i.e. the QCLs are configured to amplify different spectral regimes. By this, the different spectral regimes of the laser beam input can be enhanced one after the other in a sequential order.

Figure 6:
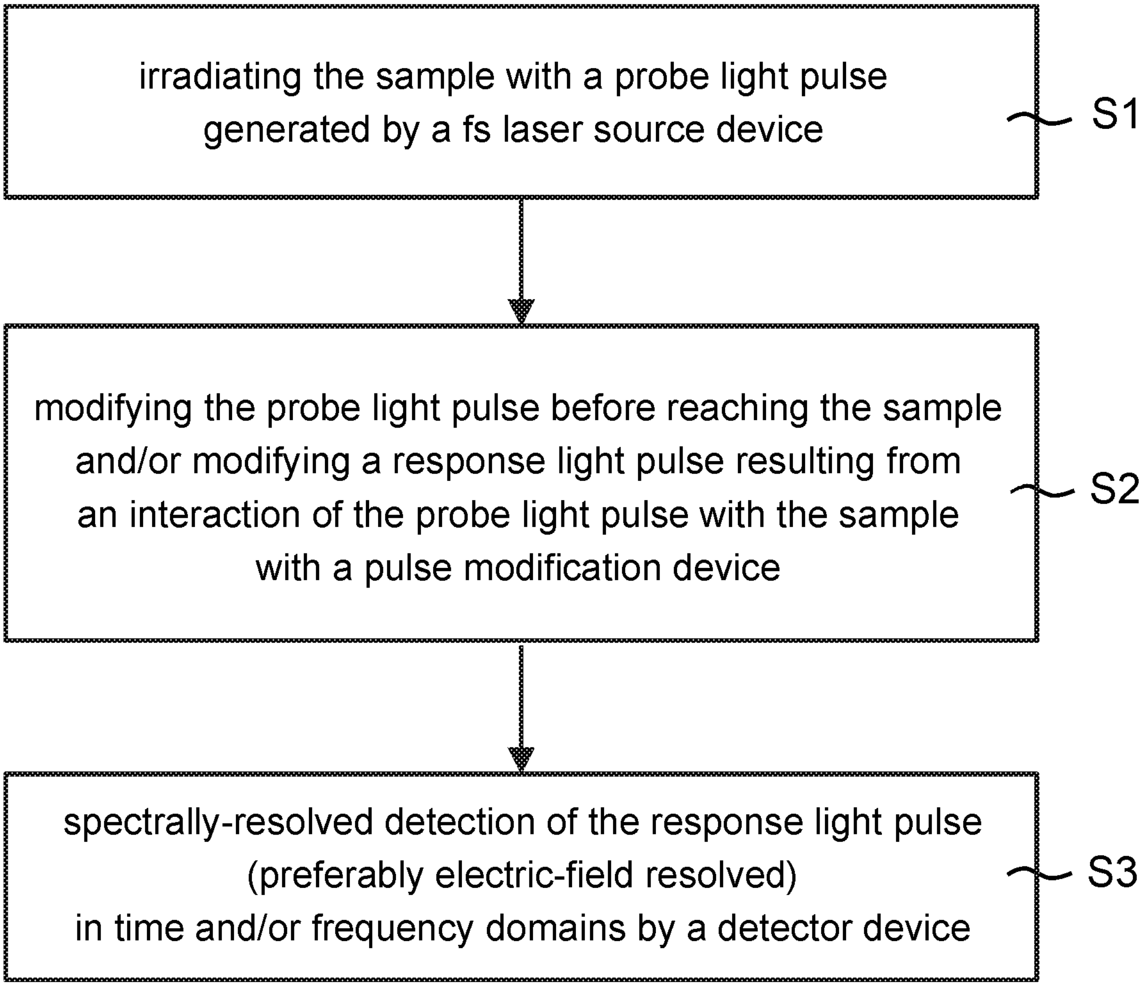
FIG. 6: a flow diagram of a method of measuring a spectral response of a sample according to an embodiment of the invention.

FIG. 6 schematically illustrates a flow chart of a method of measuring a spectral response of a sample 1 according to an embodiment of the invention. The method comprises the following steps: step S1 includes irradiating the sample 1 with a probe light pulse 2 generated by a fs laser source device 10. Step S2 then includes modifying the probe light pulse 2 before reaching the sample 1 and/or modifying a response light pulse 2' (resulting from an interaction of the probe light pulse 2 with the sample 1) with a pulse modification device 30 comprising at least one quantum cascade laser $\mathbf{3}_1$. Preferably the pulse modification device 30 comprises an array of multiple quantum cascade lasers $\mathbf{3}_1 \ldots \mathbf{3}_N$ with different centre wavelengths $\lambda_1 \ldots \lambda_N$, as described before in the context of FIGS. 3 to 5. Thereby, the step of modifying may involve amplifying one or more spectral components of the probe light pulse 2 and/or amplifying one or more spectral components of the response light pulse 2' with the at least one quantum cascade laser $\mathbf{3}_1$. For example, specific spectral regions of the probe light pulse 2 may be selectively enhanced such that the probe light pulse 2 optimally excites the sample 1. In addition or alternatively, the response light pulse 2' may be temporally enhanced in the time domain such that the molecular response, which is encoded in the wake of the main (excitation) pulse, is selectively amplified. Step S3 includes spectrally resolved detection of the response light pulse 2' by a detector device 20 in time or frequency domains (e.g., a FTIR-spectrometer, but preferably field-resolved detection with EOS).

Figure 7:
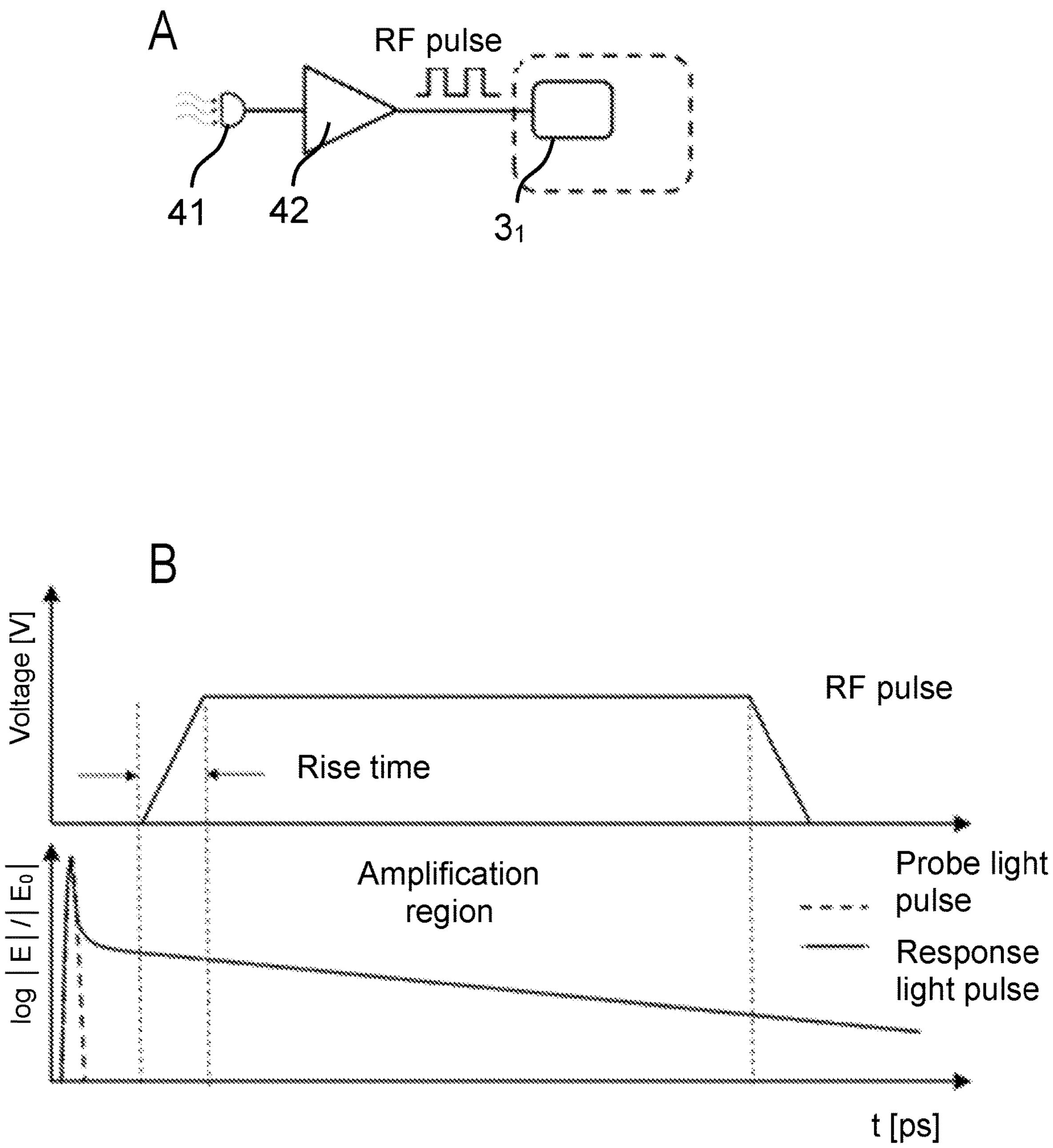
FIGS. 7 and 8: features of time-gated amplification with a QCL.
Figure 8:
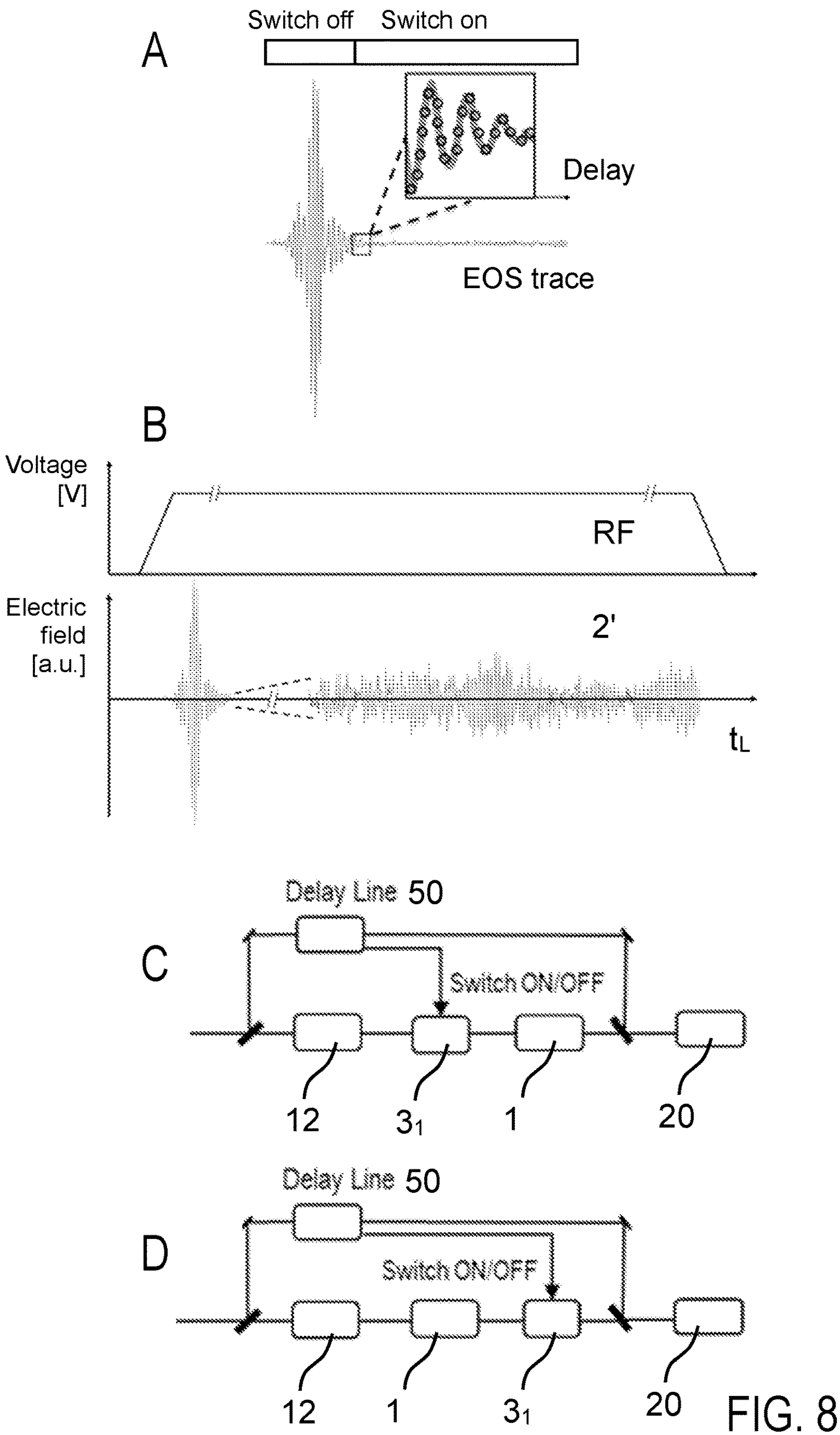

The time-gated amplification provided with the embodiments of FIG. 1 or 2 comprises an amplification achieved in a time gate (time interval). The time gate is provided by an RF pulse as outlined in the following with reference to FIGS. 7 and 8. For this process, the QCLs comprise gain switched QCLs, see for example [12]. FIGS. 7 and 8 refer in an exemplary manner to one of the QCLs of multiple QCLs only. With preferred embodiments of the invention, two applications of time-gated amplification for enhancing the contrast in a MIR measurement can be distinguished: (i) amplification of a section of the MIR waveform, preferably the temporal sample response following MIR excitation in a spectroscopic measurement; and (ii) delay-dependent MIR amplification.

The amplification of a section of the MIR waveform is illustrated in FIG. 7, which shows in FIG. 7A a schematic illustration of the time-gated amplification and in FIG. 7B a temporal shape of an RF pulse used for gating the amplification, an MIR driving pulse (dashed line) and the response light pulse 2' (solid line) coming out of the sample.

With more details, the time-gated amplification may be implemented with the control device 40 (see e. g. FIG. 2), including a radio frequency (RF) setup for generating RF pulses as the time-gating to switch on/off the gain of the QCL $\mathbf{3}_1$. The RF pulses are generated by illuminating a photodiode 41 with a fraction of the driving pulse of the mid-infrared (MIR) generation. Therefore, the switching on of the QCL $\mathbf{3}_1$ will be synchronized with the MIR probe and response pulses. The power of the RF pulse is then increased by an amplifier 42 so that the QCL $\mathbf{3}_1$ can operate above threshold, driven by the RF pulse.

The amplification dynamics for this preferred embodiment of amplifying a response light pulse is shown in an exemplary manner in FIG. 7B. The electric field E of the MIR waveform to be amplified contains the main pulse, which corresponds to the probe light pulse irradiating the sample, and the molecular response of the sample in the wake of the main pulse. The onset of the RF pulse is timed such that amplification starts after the main pulse. By fast switching on and off the RF pulse, the molecular response at the pulse tail is selectively amplified. Typical rise times of the RF pulses are currently in the 1- to 100-picosecond range. Gain switched QCL devices with 46 ps [12] and 100 ps [13] rise times of the RF pulses have been reported. These time scales are much smaller than the nanoseconds response of e. g. a gas-phase sample so that this implementation makes time-gated amplification ideal for gas-phase detection. EOS measurement in a liquid sample, which has a shorter relaxation time, are also conceivable with faster photodiodes and electronic amplifiers. As the time-gated amplification acts here in serial manner on each MIR waveform individually, this implementation is suited both for multi-shot acquisition, and for a detection scheme that measures the full EOS trace with a single laser shot.

The delay-dependent MIR amplification in a multi-pulse scanning experiment is illustrated in FIG. 8, which shows in FIG. 8A an EOS measurement controlled by the delay line 50 (see FIGS. 1, 2). Black circles represent different measurements with different time delay between sample and MIR probe light pulses. The bars on top show the temporal range where QCL $\mathbf{3}_1$ is switched on/off. FIG. 8B shows an RF pulse and an EOS trace in the laboratory time $t_L$. FIG. 8C shows a schematic setup for QCL amplification in front of the sample 1, and FIG. 8D shows a schematic setup for QCL amplification after the sample 1 (see FIGS. 1 and 2, resp.).

With more details, the delay-dependent MIR amplification acts on the full MIR waveform either of the probe light pulses before sample interaction or the response light pulses after sample interaction, with the on/off switching of amplification synchronized with the delay in a multi-pulse scanning experiment, like conventional EOS detection. In the case of EOS the measurement is performed by scanning the delay between the MIR waveform of the probe light pulse and the gate pulse and acquiring the EOS signal at each delay, generating the EOS waveform, that represents with constant amplification the MIR waveform, convolved with the instrumental response.

As shown in FIG. 8A, the measured EOS waveform consists of data points that correspond to at least one laser shot each. Depending on the detection bandwidth and scan speed, each data point may also be the time-averaged result of multiple laser shots. The time span between each data acquisition is thus at least equal or larger than the pulse-to-pulse temporal separation given by the repetition rate of the driving input laser. It is thus typically longer than multiple nanoseconds, so that time-gated amplification can be switched on and off from one data acquisition point to the next.

By switching on QCL amplification only at delays after the main pulse, it selectively enhances the signal measured for the molecular response in the wake of the pulse. In this multi-pulse application, the QCLs amplify the full MIR waveform (FIG. 8B), but the delay-dependence of the amplification leads to an increased sample response signal in the EOS waveform measured by the detector device 20 (FIG. 8B). This application of time-gating is not limited by the time scale of the sample response, and applicable also to picosecond or shorter MIR waveforms.

FIGS. 8C and 8D show two preferred embodiments, wherein in the first embodiment (FIG. 8C) the QCL $\mathbf{3}_1$ amplifies the MIR probe light pulse received for the DFG unit 12 before the sample 1 and is switched on/off depending on the delay of the sample pulse (gate pulse). Amplification can still be additionally triggered by RF pulses synchronized with the MIR waveforms to increase amplification efficiency [14]. The delay scan corresponds to a change of the optical delay of the gate pulse with respect to the MIR probe light pulse, for example with a mechanical change of the optical path length (mechanical stage) or with acousto-optic modulation in the delay line 50 [15].

In the other embodiment (FIG. 8C), QCL amplification takes place after the sample 1, thus amplifying both the residual excitation probe laser pulse and the sample response laser pulse, with the same delay-control of the amplification as in the embodiment of FIG. 8C.

The features of the invention disclosed in the above description, the drawing and the claims can be of significance both individually as well as in combination or sub-combination for the realisation of the invention in its various embodiments.

The invention claimed is:

1. Spectroscopic measuring apparatus (100) being configured for measuring a spectral response of a sample (1), comprising:

a fs laser source device (10) being arranged for an irradiation of the sample (1) with a sequence of probe light pulses (2) having a primary spectrum; and a detector device (20) being arranged for a temporally and/or spectrally resolved detection of response light pulses (2') having an altered spectrum and/or temporal structure and resulting from an interaction of the probe light pulses (2) with the sample (1), characterized by a pulse modification device (30) comprising at least one quantum cascade laser ($\mathbf{3}_1 \ldots \mathbf{3}_N$), wherein the pulse modification device (30) is configured to shape a temporal profile of the response light pulses (2') by time-gate amplifying of one or more spectral components of the response light pulses (2') with the at least one quantum cascade laser ($\mathbf{3}_1 \ldots \mathbf{3}_N$).

2. Spectroscopic measuring apparatus according to claim 1, wherein the at least one quantum cascade laser ($\mathbf{3}_1 \ldots \mathbf{3}_N$) comprises an array of multiple quantum cascade lasers ($\mathbf{3}_1 \ldots \mathbf{3}_N$) with different centre wavelengths ($\lambda_1 \ldots \lambda_N$).

3. Spectroscopic measuring apparatus according to claim 2, wherein a) the multiple quantum cascade lasers ($\mathbf{3}_1 \ldots \mathbf{3}_N$) are arranged in a parallel configuration; and/or b) the pulse modification device (30) comprises a splitter device (31) configured to spatially separate a laser beam input into several sub-beams with different spectral intervals;

a relaying device (32) configured to direct each of the sub-beams to one of the multiple quantum cascade lasers ($\mathbf{3}_1 \ldots \mathbf{3}_N$) respectively; and a combiner device (33) configured to collimate an amplified output of each of the multiple quantum cascade lasers ($\mathbf{3}_1 \ldots \mathbf{3}_N$) into a single laser beam output.

4. Spectroscopic measuring apparatus according to claim 2, wherein a) the multiple quantum cascade lasers ($\mathbf{3}_1 \ldots \mathbf{3}_N$) are arranged in a sequential configuration; and/or b) the pulse modification device (30) comprises a relaying device (32') configured to direct a laser beam input in a consecutive order to each of the multiple quantum cascade lasers ($\mathbf{3}_1 \ldots \mathbf{3}_N$).

5. Spectroscopic measuring apparatus according to claim 2, wherein a first QCL-subset of the multiple quantum cascade lasers ($\mathbf{3}_1 \ldots \mathbf{3}_N$) is arranged in a parallel configuration and a second QCL-subset of the multiple quantum cascade lasers ($\mathbf{3}_1 \ldots \mathbf{3}_N$) is arranged in a sequential configuration.

6. Spectroscopic measuring apparatus according to claim 2, wherein the least one quantum cascade laser ($\mathbf{3}_1$) has an output power of at least 1 Watt and/or a centre wavelength in the range between 3 μm and 24 μm.

7. Spectroscopic measuring apparatus according to claim 2, further comprising a control device (40) being configured to control the pulse modification device (30) to generate a predefined spectral and/or temporal profile of the the response light pulses (2').

8. Spectroscopic measuring apparatus according to claim 2, wherein the fs laser source device (10) is adapted for generating the probe light pulses (2) with at least one of the features:

the probe light pulses (2) comprise ultra-broadband mid-infrared pulses;

the probe light pulses (2) have a pulse duration below 100 fs;

the probe light pulses (2) have an average power above 10 mW;

the primary spectrum covers at least one frequency octave;

the primary spectrum covers a wavelength range from 5 μm to 15 μm; and the primary spectrum is a continuous or quasi-continuous spectrum.

9. Method of measuring a spectral and/or temporal response of a sample (1), upon excitation with probe light pulses (2), comprising the steps:

irradiating the sample (1) with a sequence of the probe light pulses (2) generated by a fs laser source device (10), wherein the probe light pulses (2) have a primary spectrum, and spectrally and/or temporally resolved detection of response light pulses (2') by a detector device (20), wherein the response light pulses (2') have an altered spectrum resulting from an interaction of the probe light pulses (2) with the sample (1);

characterized by a step of modifying the response light pulses (2') with a pulse modification device (30) comprising at least one quantum cascade laser ($3_1$ . . . $3_N$), wherein the modifying comprises shaping. with the pulse modification device (30), a temporal profile of the response light pulses (2') by time-gated amplification of one or more spectral components of the response light pulses (2') with the at least one quantum cascade laser ($3_1$ . . . $3_N$).

10. Method according to claim 9, wherein the response light pulses (2') are modified before reaching the detector device (20).

11. Method according to claim 9, wherein the at least one quantum cascade laser ($3_1$) comprises an array of multiple quantum cascade lasers ($3_1$ . . . $3_N$) with different centre wavelengths ($\lambda_1$ . . . $\lambda_N$).

12. Method according to claim 11, wherein a) the multiple quantum cascade lasers ($3_1$ . . . $3_N$) are arranged in a parallel configuration; and/or b) the step of modifying includes:

splitting the at least one of the probe light pulses (2) and the response light pulses (2') by a splitter device (31) into several sub-beams with different spectral intervals;

directing each of the sub-beams to one of the several quantum cascade lasers ($3_1$ . . . $3_N$) respectively by a relaying device (32); and collimating an amplified output of each of the multiple quantum cascade lasers ($3_1$ . . . $3_N$) into a single laser beam output by a combiner device (33).

13. Method according to claim 11, wherein a) the multiple quantum cascade lasers ($3_1$ . . . $3_N$) are arranged in a sequential configuration; and/or b) the step of modifying includes:

directing the response light pulses (2') in a consecutive order to each of the several quantum cascade lasers ($3_1$ . . . $3_N$) by a relaying device (32').

14. Method according to claim 11, wherein a first QCL-subset of the multiple quantum cascade lasers ($3_1$ . . . $3_N$) is arranged in a parallel configuration and a second QCL-subset of the multiple quantum cascade lasers ($3_1$ . . . $3_N$) is arranged in a sequential configuration.

15. Method according to claim 9, wherein the least one quantum cascade laser ($3_1$ . . . $3_N$) has an output power of at least 1 Watt and/or a centre wavelength in the range between 3 μm and 24 μm.

16. Method according to claim 9, further comprising the step of determining at least one spectral region of interest, wherein the step of modifying includes increasing a power spectral density in the spectral region of interest.

17. Method according to claim 9, further comprising the step of defining a target spectral and/or temporal profile of the response light pulses (2, 2'); and controlling the pulse modification device (30) by a control device (40) based on the defined target spectral and/or temporal profile.

18. Method according to claim 9, wherein the probe light pulses (2) have at least one of the features the probe light pulses (2) comprise an ultra-broadband mid-infrared pulses;

the probe light pulses (2) have a pulse duration below 100 fs;

the probe light pulses (2) have an average power above 10 mW;

the primary spectrum covers at least one frequency octave;

the primary spectrum covers a wavelength range from 5 μm to 15 μm; and the primary spectrum is a continuous or quasi-continuous spectrum.

* * * * *